US010551284B2

(12) United States Patent
Baxter et al.

(10) Patent No.: US 10,551,284 B2
(45) Date of Patent: Feb. 4, 2020

(54) SAMPLING PROBE APPARATUS FOR COLLECTING A SAMPLE OF A GAS STREAM CONTAINING PARTICULATE MATTER AND METHOD OF USING THE SAME

(71) Applicant: Dust Company, Inc., Raleigh, NC (US)

(72) Inventors: Robert Wyatt Baxter, Raleigh, NC (US); Derrick James Hinkle, Louisburg, NC (US)

(73) Assignee: Dust Company, Inc., Raleigh, NC (US)

( * ) Notice: Subject to any disclaimer, the term of this patent is extended or adjusted under 35 U.S.C. 154(b) by 0 days.

(21) Appl. No.: 15/597,526

(22) Filed: May 17, 2017

(65) Prior Publication Data

US 2017/0336302 A1   Nov. 23, 2017

Related U.S. Application Data

(60) Provisional application No. 62/337,653, filed on May 17, 2016.

(51) Int. Cl.
*G01N 1/22* (2006.01)
*G01N 1/44* (2006.01)
*G01N 15/14* (2006.01)

(52) U.S. Cl.
CPC ............. *G01N 1/2247* (2013.01); *G01N 1/44* (2013.01); *G01N 15/1404* (2013.01); *G01N 2001/2264* (2013.01)

(58) Field of Classification Search
CPC .......... G01N 1/22; G01N 1/2247; G01N 1/44; G01N 15/14; G01N 15/1404;
(Continued)

(56) References Cited

U.S. PATENT DOCUMENTS 2,461,584 A * 2/1949 Andersen ................ B07B 4/025
159/4.01
3,784,902 A   1/1974 Huber
(Continued)

FOREIGN PATENT DOCUMENTS

DE       277378 A3    4/1990
JP    H0915118 A      1/1997
JP    H09318501 A    12/1997

OTHER PUBLICATIONS

International Search Report and the Written Opinion of the International Searching Authority corresponding to International Patent Application No. PCT/US2017/033050(13 pages) (dated Jul. 28, 2017).

*Primary Examiner* — Jamil Ahmed
(74) *Attorney, Agent, or Firm* — Myers Bigel, P.A.

(57) ABSTRACT

An apparatus includes a sampling probe having a first portion and a second portion. The first portion is configured to penetrate inside a wall of a duct having an inner chamber that is configured to carry a gas stream containing particulate matter therethrough. The first portion is further configured to divert a sample of the gas stream from the inner chamber of the duet to the second portion that extends from the wall of the duct opposite the inner chamber. The second portion of the sampling probe is configured to direct the sample of the gas stream in a first direction with a second direction corresponding to a direction of the gravitational force of the earth. A first ray corresponding to the first direction forms an angle β with a second ray corresponding to the second direction. The angle β is less than 90 degrees.

25 Claims, 4 Drawing Sheets

(58) Field of Classification Search
CPC ............ G01N 2001/2264; A61K 49/06; A61K 49/18; G01R 33/28; G01R 33/282; C01B 23/00; C01B 23/0036; B07B 4/00; B07B 4/025

See application file for complete search history.

(56) References Cited

U.S. PATENT DOCUMENTS

| | | | |
|---|---|---|---|
| 4,034,611 A | | 7/1977 | Horling |
| 4,657,667 A | | 4/1987 | Etkin |
| 5,975,309 A | * | 11/1999 | Mitsuda .................... B03B 4/00 209/138 |
| 6,151,953 A | * | 11/2000 | Patashnick ............. G01N 15/02 73/28.01 |
| 6,481,299 B2 | | 11/2002 | Silvis et al. |
| 2010/0315638 A1 | * | 12/2010 | Goohs .................. G01N 21/274 356/337 |
| 2017/0056532 A1 | * | 3/2017 | Freeman ................ A61K 49/18 |

* cited by examiner

SAMPLING PROBE APPARATUS FOR COLLECTING A SAMPLE OF A GAS STREAM CONTAINING PARTICULATE MATTER AND METHOD OF USING THE SAME

CROSS-REFERENCE TO RELATED APPLICATION

The present application claims priority to U.S. Provisional Patent Application Ser. No. 62/337,653, filed May 17, 2016, the entire content of which is incorporated by reference herein as if set forth in its entirety.

BACKGROUND

The present disclosure relates generally to particulate discharge and, more particularly, to methods, systems, and apparatus that can be used to monitor particulate discharge for both manual and continuous applications.

A variety of suspended particles may be found in a typical atmosphere whether indoor or outdoor. Size, chemical composition, concentration, and temporal variability all have the potential to affect public health and perception of pollution. As a result, particulate monitoring systems, devices, or instruments are becoming more prevalent in both process and environmental applications. Conventional sampling probes used in particulate monitoring systems, devices, or instruments are configured so as to extend upwards away from the ground. FIG. 1 is a diagram that illustrates a conventional sampling probe used to divert a sample of a gas stream containing particulate matter (PM) for evaluating the concentration of the particulate matter in the gas stream. As shown in FIG. 1, a stack or duct 105 has a gas that flows therethrough and contains PM 110. A probe 115 is configured to extend into the gas stream and divert a sample of the gas stream to a particulate matter analysis component 125 to evaluate the concentration of the PM in the stream. As shown in FIG. 1, an angle α formed by a ray corresponding to the direction of the gas flow through the probe 115 and a ray corresponding to the direction of the earth's gravitational force is greater than 90 degrees. As a result, in continuous particulate monitoring systems, for example, PM that is deposited in the probe 115 may not be detected by the particulate matter analysis component 125, which may bias the results of the PM concentration determination. Conventional particulate monitoring systems, devices, or instruments may use cyclonic heating to remove moisture from PM before evaluating the concentration of, the particulate matter with a detector. Processing the sampled gas flow with a cyclonic heater may result in further loss of PM as it is common for a portion of the PM to become trapped in the cyclonic) heater. While configuring the probe 115 as shown in FIG. 1 to take advantage of the effects of gravity pulling water droplets back towards the main gas flow in the stack or duct 105 may allow the probe 115 to self-clean, particulate matter from a sample may nonetheless be lost affecting the accuracy of a PM concentration determination.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the disclosure.

Some embodiments of the inventive concept provide an apparatus, comprising: a sampling probe having a first portion and a second portion. The first portion is configured to penetrate inside a wall of a duct having an inner chamber that is configured to carry a gas stream containing particulate matter therethrough. The first portion is further configured to divert a sample of the gas stream from the inner chamber of the duct to the second portion that extends from the wall of the duct opposite the inner chamber. The second portion of the sampling probe is configured to direct the sample of the gas stream in a first direction with a second direction corresponding to a direction of the gravitational force of the earth. A first ray corresponding to the first direction forms an angle β with a second ray corresponding to the second direction. The angle β is less than 90 degrees.

In other embodiments, the angle β is less than 80 degrees.

In still other embodiments, the angle β is less than 45 degrees.

In still other embodiments, the angle β is approximately 0 degrees.

In still other embodiments, the inner chamber of the duct is configured to carry the gas stream in a third direction that is substantially opposite that of the second direction.

In still other embodiments, the inner chamber of the duct is configured to carry the gas stream in a third direction that is substantially perpendicular to that of the second direction.

In still other embodiments, the apparatus further comprises a particulate matter analysis component that is configured to receive the sample of the gas stream from the second portion of the sampling probe and comprises a detector module that is configured to determine a concentration of the particulate matter in the sample of the gas stream.

In still other embodiments, the detector is configured to perform a least one of a scattered light measurement analysis on the sample of the gas stream and a transmissiometry analysis on the sample of the gas stream.

In still other embodiments, the particulate matter analysis component further comprises at least one of a heater/vaporizer module, a dilution module, a water spray module, and an air pulse module.

In still other embodiments, the heater/vaporizer module is configured to remove moisture from the sample of the gas stream before the sample of the gas stream is provided to the detector module.

In still other embodiments, the dilution module is configured to dilute the concentration of the particulate matter in the sample of the gas stream before the sample of the gas stream is provided to the detector module.

In still other embodiments, the water spray module is configured to add moisture to the sample of the gas stream before the sample of the gas stream is provided to the detector module.

In still other embodiments, the air pulse module is configured to push the sample of the gas stream with pulses of air to adjust a velocity of the sample of the gas stream before the sample of the gas stream is provided to the detector module.

In still other embodiments, the apparatus further comprises an outlet probe that is configured to return the sample of the gas stream output from the particulate matter analysis component to the duct.

Some embodiments of the inventive concept provide a method, comprising: diverting a sample of a gas stream from an inner chamber of a duct using a sampling probe. The inner chamber of the duct is configured to carry the gas stream containing particulate matter therethrough. The sampling probe has a first portion configured to penetrate inside a wall of the duct to the inner chamber and a second portion that extends from the wall of the duct opposite the inner chamber. The method further comprises determining a concentration of the particulate matter in the sample of the gas stream. The second portion of the sampling probe is configured to direct the sample of the gas stream in a first direction with a second direction corresponding to a direction of the gravitational force of the earth. A first ray corresponding to the first direction forms an angle β with a second ray corresponding to the second direction. The angle β is less than 90 degrees.

In further embodiments, the angle β is less than 80 degrees.

In still further embodiments, the angle β is less than 45 degrees.

In still further embodiments, the angle β is approximately 0 degrees.

In still further embodiments, the inner chamber of the duct is configured to carry the gas stream in a third direction that is substantially opposite that of the second direction.

In still further embodiments, the inner chamber of the duct is configured to carry the gas stream in a third direction that is substantially perpendicular to that of the second direction.

In still further embodiments, the method further comprises: performing at least of a scattered light measurement analysis on the sample of the gas stream and a transmissiometry analysis on the sample of the gas stream.

In still further embodiments, the method further comprises: removing moisture from the sample of the gas stream before determining the concentration of the particulate matter in the sample of the gas stream.

In still further embodiments, the method further comprises: diluting the concentration of the particulate matter in the sample of the gas stream before determining the concentration of the particulate matter in the sample of the gas stream.

In still further embodiments, the method further comprises: adding moisture to the sample of the gas stream before determining the concentration of the particulate matter in the sample of the gas stream.

In still further embodiments, the method further comprises: pushing the sample of the gas stream with pulses of air to adjust a velocity of the sample of the gas stream before determining the concentration of the particulate matter in the sample of the gas stream.

Other methods, systems, and/or apparatus according to embodiments of the invention will be or become apparent to one with skill in the art upon review of the following drawings and detailed description. It is intended that all such additional methods, systems, and/or apparatus be included within this description, be within the scope of the present invention, and be protected by the accompanying claims. It is noted that aspects of the invention described with respect to one embodiment, may be incorporated in a different embodiment although not specifically described relative thereto. That is, all embodiments and/or features of any embodiment can be combined in any way and/or combination.

BRIEF DESCRIPTION OF THE DRAWINGS

Other features of exemplary embodiments will be more readily understood from the following detailed description of specific embodiments thereof when read in conjunction with the accompanying drawings, in which.

DETAILED DESCRIPTION

Figure 1:
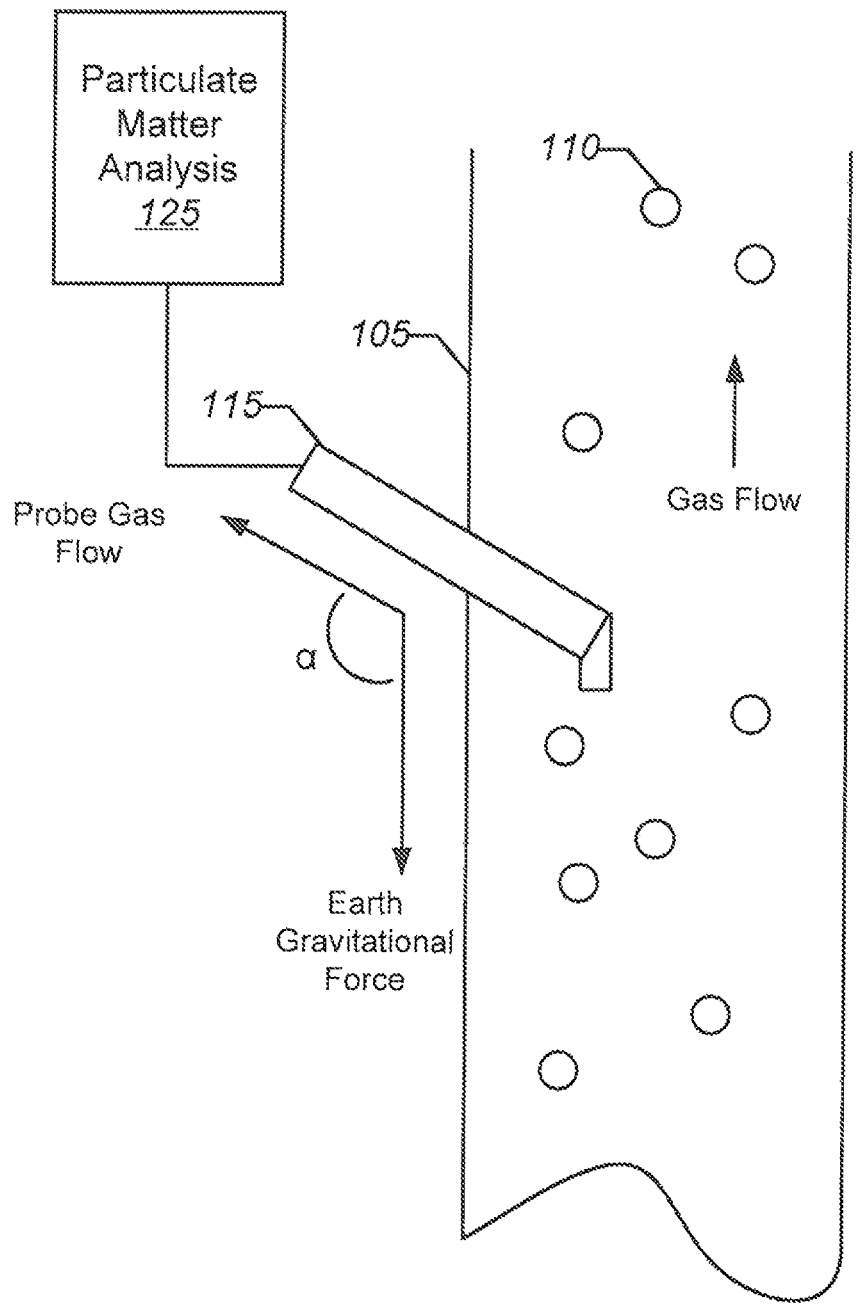
FIG. 1 is a diagram that illustrates a conventional sampling probe used to divert a sample of a gas stream containing particulate matter for evaluating the concentration of the particulate matter in the gas stream.

While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like reference numbers signify like elements throughout the description of the figures.

As used herein, the singular forms "a," "an," and "the" are intended to include the plural forms as well, unless expressly stated otherwise. It should be further understood that the terms "comprises" and or "comprising" when used in this specification is taken to specify the presence of stated features, integers, steps, operations, elements, and/or components, but does not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Embodiments are described herein with respect to a gas stream that contains a particulate material. It will be understood that the particulate material is not limited to any type of material and may include, but is not limited to, solid materials, particles, dust, ash, fly ash, and the like.

Some embodiments of the inventive concept described herein stem from a realization that a particulate matter (PM) sampling probe, according to some embodiments of the inventive concept, may be engineered for improved PM transport to ensure that a more representative sample of the PM entering the nozzle of the probe is ultimately transported to the detector or detection device. In accordance with various embodiments of the inventive concept, a probe may be configured with a structural geometry to improve transport of the PM in a sample of a gas stream through the probe and into a particulate matter analysis component that includes a detector or detection device, which is configured to determine the PM concentration in the gas stream. In some embodiments, a sampling probe may include a transport line portion that is sloped downward to facilitate the suspension of the PM in the sample of the gas stream so as to reduce the amount of PM that is trapped in the sampling probe or other components of a particular matter analysis component before the sampled gas stream reaches the detector or detection device. Large density PM transported within conventional PM monitoring systems using horizontal or upward sloping probes may be negatively affected by the force of gravity such that PM is "pulled" to the lower part of the transport line where gas velocities may be lower. As a result, large particles may not get detected by the particulate monitoring system. These large particles may be more representative of the PM mass in the sampled gas stream.

Smaller particles (e.g., 0.3-0.5 microns or less) may not be significantly affected by gravity, but can be affected by van der Waals forces (static charges). These forces on smaller particles can cause them to attach to the walls of the sampling probe or other elements of the particulate matter analysis component. Thus, in some embodiments of the inventive concept, the sample of the gas stream may be diluted with air, have moisture added thereto, heated to remove moisture, and/or pushed with air pulses to maintain a particular flow velocity. These manipulations of the sample of the gas stream may be designed in concert with the slope angle of the sampling probe to reduce the amount of PM that is lost in the sampling probe and/or other elements of the particulate matter analysis component. The particular points in the processing of the sample of the gas stream at which these various manipulations (e.g., dilution, moisture, heat, air pulse) may be applied may be depend on the specific application that is being analyzed.

Figure 2:
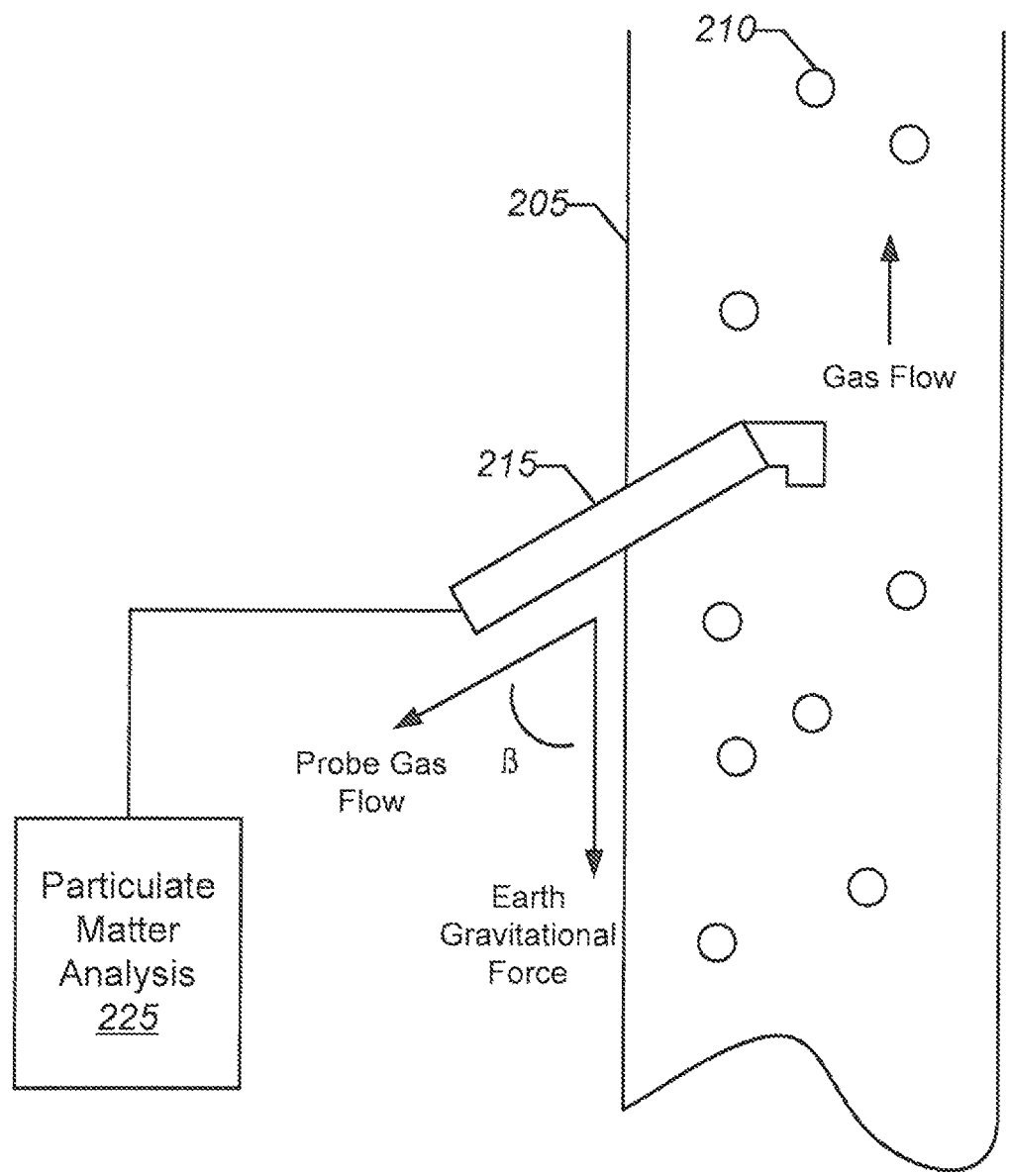
FIG. 2 is a diagram that illustrates a sampling probe used to divert a sample of a gas stream containing particulate matter for evaluating the concentration of the particulate matter in the gas stream according to some embodiments of the inventive concept.

FIG. 2 is a diagram that illustrates a sampling probe used to divert a sample of a gas stream containing particulate matter for evaluating the concentration of the particulate matter in the gas stream according to some embodiments of the inventive concept.

As shown in FIG. 2, a stack or duct 205 has a gas that flows therethrough and contains PM 210. A sampling probe 215 comprises a first portion that extends inside the wall of the duct 205 where the gas flow is carried in the inner chamber of the duct. The end of the first portion of the sampling probe 215 includes a nozzle that is designed to divert a sample of the gas flow including the PM into the sampling probe 215. The sampling probe 215 further comprises a second portion that extends from the wall of the duct 205 opposite the inner chamber. The first portion and second portion of the sampling probe 215 cooperate to transport the sample of the gas flow to the particulate matter analysis component 225, which is configured to evaluate the concentration of the PM in the sample of the gas stream. In some embodiments of the inventive concept, an angle β formed by a ray corresponding to the direction of the gas flow through the second portion of the sampling probe 215 and a ray corresponding to the direction of the earth's gravitational force is less than 90 degrees. That is, the sampling probe 215 is configured to take advantage of the earth's gravitational pull to ensure that PM flows down the slope of the sampling probe 215 towards the particulate matter analysis component 225. Thus, in some embodiments, the particulate matter analysis component 225, including the PM detector or detection device, is positioned lower relative to the sampling probe 215 with respect to the earth's sea level.

Depending on particle size, the saltation velocity associated with the PM in the flow of the sampled gas, and the actual velocity of the flow of the sampled gas, the angle β may be adjusted to reduce the amount of PM that is trapped in the sampling probe 215. In general, larger size PM has a higher saltation velocity, which may benefit from the sampling probe 215 having a steeper slope. Thus, in some embodiments, the angle β is less than 80 degrees and in other embodiments, the angle β is less than 45 degrees. Moreover, in some embodiments, at least a portion of the first portion of the sampling probe 215, which is disposed in the inner chamber of the duct 205, may direct the sample of the gas stream in the same direction as the second portion of the sampling probe 215 thereby having the same angular relationship with the earth's gravitational force.

Figure 3A:
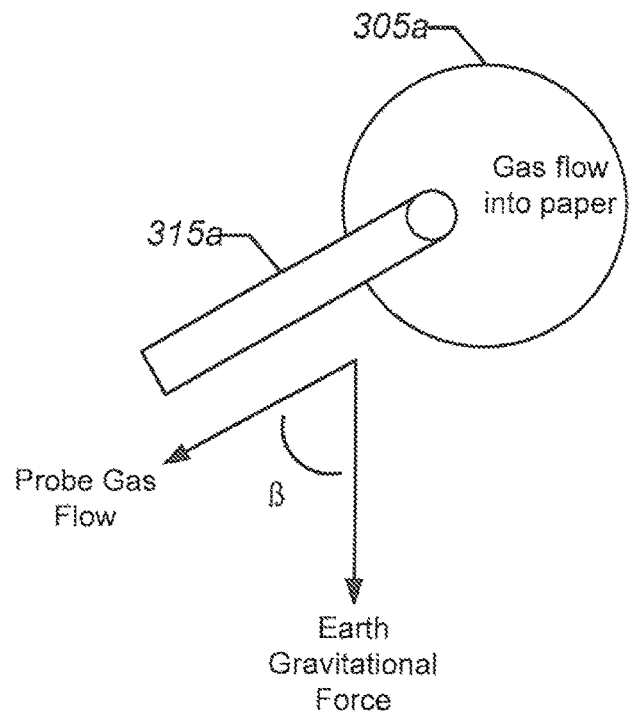
FIGS. 3A and 3B are diagrams that illustrate different configurations between the sampling probe and the duct or stack carrying the gas stream according to some embodiments of the inventive concept.
Figure 3B:
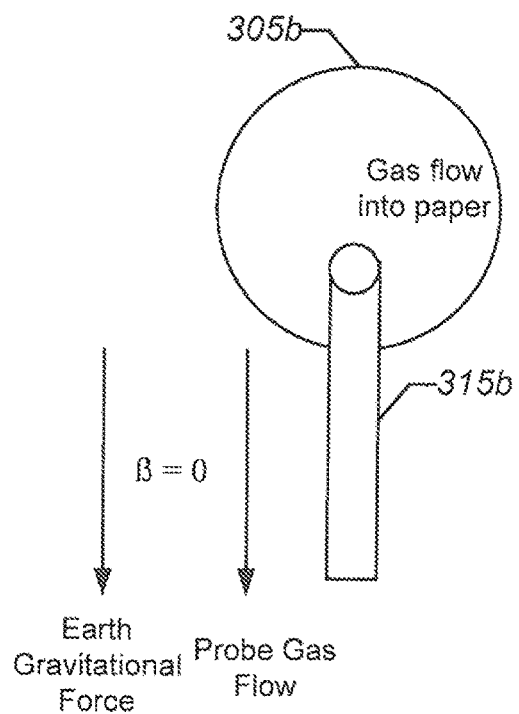

FIG. 2 illustrates a duct or stack 205 that is configured to with a vertical gas flow, i.e., opposite the direction of the earth's gravitational force. Embodiments of the inventive concept are also applicable to other configurations in which the duct or stack transports the gas stream containing the PM in other directions. As shown in FIG. 3A, the duct or stack 305a transports the gas stream containing the PM in a direction into the paper that is substantially perpendicular to the direction of the earth's gravitational force. The sampling probe 315a may be configured similarly to that of the sampling probe 215 of FIG. 2 such that the angle β formed by a ray corresponding to the direction of the gas flow through the second portion of the sampling probe 315a and a ray corresponding to the direction of the earth's gravitational force is less than 90 degrees. Referring now to FIG. 3B, the duct or stack 305b also transports the gas stream containing the PM in a direction into the paper that is substantially perpendicular to the direction of the earth's gravitational force. The sampling probe 315b, however, is configured so as to transport that sampled gas stream in a direction that is substantially parallel to a direction of the earth's gravitational force. As a result, the angle β formed by a ray corresponding to the direction of the gas flow through the second portion of the sampling probe 315b and a ray corresponding to the direction of the earth's gravitational force is approximately 0 degrees.

Figure 4:
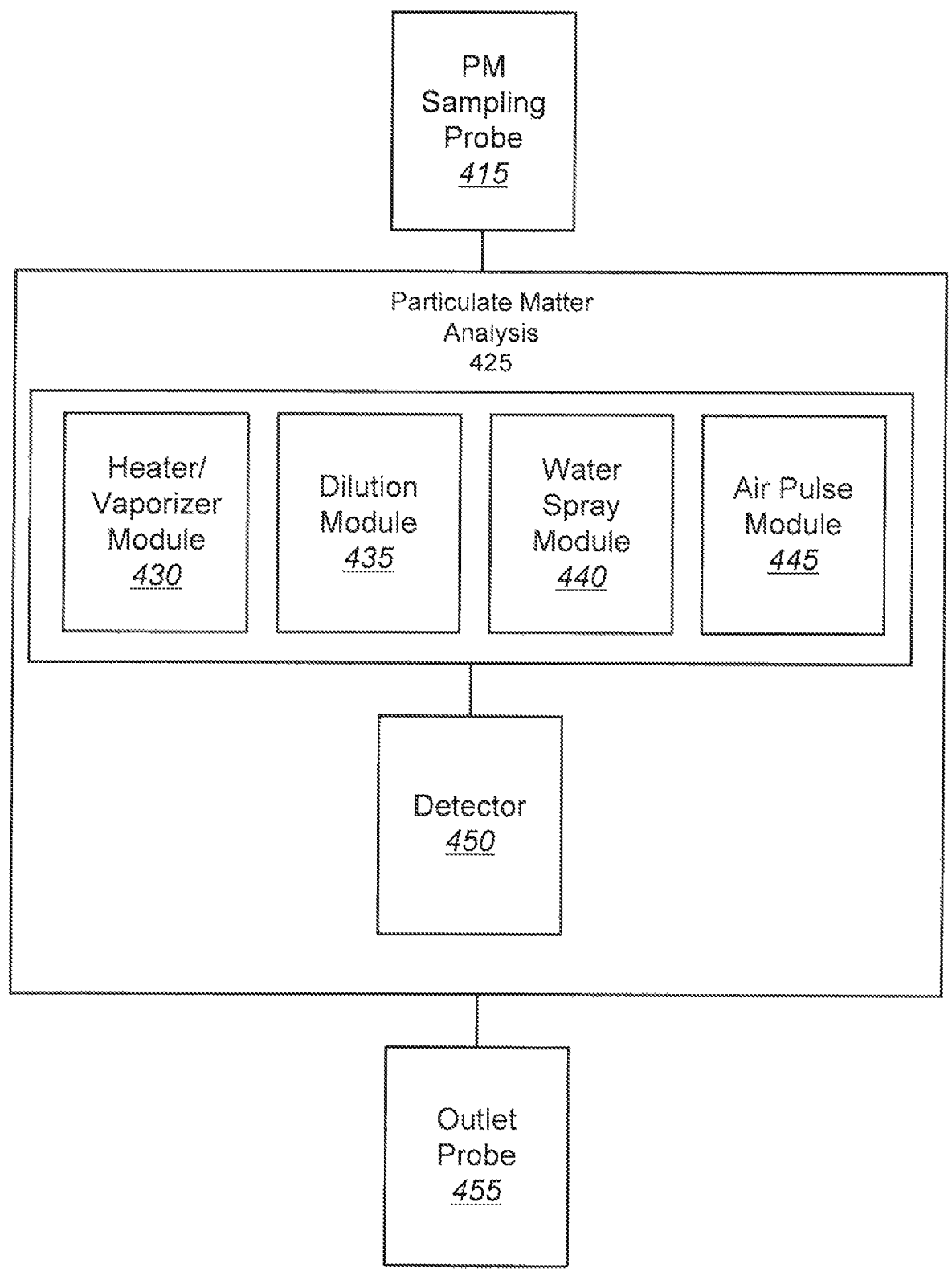
FIG. 4 is a block diagram of the sampling probe and the particulate matter analysis component according to some embodiments of the inventive concept.

FIG. 4 is a block diagram of the sampling probe and the particulate matter analysis component according to some embodiments of the inventive concept. As shown in FIG. 4, the PM sampling probe 415 is coupled to a particulate matter analysis component 425, which is coupled to an outlet probe 455. The PM sampling probe 415 may be embodied as any of the sampling probes 215, 315a, and 315b described above. The PM sampling probe 415 is configured to extend into a gas stream earned through the inner chamber of a duct or stack and divert a sample of the gas stream to the particulate matter analysis component 425 to evaluate the concentration of the PM in the stream. The particulate matter analysis component 425 may include various modules that can manipulate the sampled gas stream to prepare the gas stream for the detector 450. As shown in FIG. 4, the particulate matter analysis component 425 comprises a heater/vaporizer module 430, a dilution module 435, a water spray module 440, and, an air pulse module 445. The heater/vaporizer module 430 may be configured to remove moisture from the sample of the gas stream before the sample of the gas stream is provided to the detector module 450. The dilution module 435 may be configured to dilute the concentration of the PM in the sample of the gas stream before the sample of the gas stream is provided to the detector module 450. The water spray module 440 is configured to add moisture to the sample of the gas stream before the sample of the gas stream is provided to the detector module 450. The air pulse module 445 is configured to push the sample of the gas stream with pulses of air to adjust a velocity of the sample of the gas stream before the sample of the gas stream is provided to the detector module 450. These various modules may apply their functionality at various points in the path between the collection of the sampled gas stream from the duct or stack until the sampled gas stream reaches the detector module 450. The point of addition may depend, for example, on the specific, application. Moreover, these modules may be used in concert with the slope angle of the PM sampling probe 415 to reduce the amount of PM that is lost in the sampling probe 415 or other elements of the particulate matter analysis component 425 before the sampled gas is provided to the detector 450. For example, the heater/vaporizer module 430 may be used to ensure that any water droplets are removed before the sampled gas reaches the detector 450 for a determination of the PM concentration. But the heat and cyclonic action of the heater/vaporizer module 430 may cause some PM to impact the sidewalls of the cyclonic heater/vaporizer unit, which may cause these particles to be lost. As a result, the system may be designed to reduce the amount of additional PM that is lost from the stream in other elements of the system. For example, the slope of the sampling probe may be increased to take advantage of the earth's gravitational pull in transporting PM to the particulate matter analysis module 435. The air pulse module 445 may be used to ensure the velocity of the PM in the sampled gas stream does not fall below the saltation velocity.

Which of the particular techniques, i.e., heating, dilution, water spray, and/or air pulse, are applied to a sample gas stream may depend on the application or detector module 450 type. If the detector module 450 filters the PM from the sampled gas stream using, for example, beta attenuation, then any of the techniques may be applied to the sampled gas stream with a goal to ensure that the gas stream provided to the detector module 450 is substantially devoid of water particles. If the detector module 450 determines the concentration of the PM in the sampled stream without filters, then some of the techniques may be used depending on the application. For example, certain techniques, such as air dilution via the dilution module 435, may result in the sampled gas stream having a PM concentration that is below a detectable level depending on the technology used in the detector module 450.

The detector module 450 may determine the concentration of the PM in the sampled gas stream in various ways in accordance with different embodiments of the inventive concept. In some embodiments, the detector module 450 may perform at least one of a scattered light measurement analysis on the sampled gas stream and a transmissiometry analysis, on the sampled gas stream. Scattered light measurement analysis is a technique in which a light sender transmits light, which is scattered in the gas stream by the particles and recorded by a sensitive receiver. Transmissiometry analysis is a technique in which light shines through a mixture of gas and particles whose intensity is weakened by the particles. The more particles are located in the light beam, the more the light is weakened.

The particulate matter analysis component 425 provides the sampled gas stream to the outlet probe 455, which is configured to return the sampled gas stream to the duct or stack.

Embodiments of the inventive concept may provide a PM sampling probe that can ensure that the sampled gas stream that is presented to a detector for analysis of the PM concentration is more representative of the stream flowing through inner chamber of the duct or stack from which the sample was obtained. This may be achieved through use of particular angles, system velocities, and techniques that reduce the loss of PM in both the sampling probe and the particulate matter analysis component.

Many variations and modifications can be made to the preferred embodiments without substantially departing from the principles of the present invention. All such variations and modifications are intended to be included herein within the scope of the present invention, as set forth in the following claims.

That which is claimed:

1. An apparatus, comprising:
   a sampling probe having a first portion and a second portion, the first portion being configured to penetrate inside a wall of a duct having an inner chamber that is configured to carry a gas stream containing particulate matter therethrough and being further configured to divert a sample of the gas stream from the inner chamber of the duct to the second portion that extends from the wall of the duct opposite the inner chamber, the gas stream and the sample of the gas stream having a same particulate matter concentration;
   wherein the second portion of the sampling probe is configured to direct the sample of the gas stream in a first direction with a second direction corresponding to a direction of the gravitational force of the earth;
   wherein a first ray corresponding to the first direction forms an angle β with a second ray corresponding to the second direction; and
   wherein the angle β is less than 90 degrees.

2. The apparatus of claim 1, wherein the angle β is less than 80 degrees.

3. The apparatus of claim 1, wherein the angle β is less than 45 degrees.

4. The apparatus of claim 1, wherein the angle β is approximately 0 degrees.

5. The apparatus of claim 1, wherein the inner chamber of the duct is configured to carry the gas stream in a third direction that is substantially opposite that of the second direction.

6. The apparatus of claim 1, wherein the inner chamber of the duct is configured to carry the gas stream in a third direction that is substantially perpendicular to that of the second direction.

7. The apparatus of claim 1, further comprising:
   a particulate matter analysis component that is configured to receive the sample of the gas stream from the second portion of the sampling probe and comprises a detector module that is configured to determine a concentration of the particulate matter in the sample of the gas stream received from the second portion of the sampling probe.

8. The apparatus of claim 7, wherein the detector is configured to perform at least one of a scattered light measurement analysis on the sample of the gas stream received from the second portion of the sampling probe and a transmissiometry analysis on the sample of the gas stream received from the second portion of the sampling probe.

9. The apparatus of claim 7, wherein the particulate matter analysis component further comprises at least one of a heater/vaporizer module, a dilution module, a water spray module, and an air pulse module.

10. The apparatus of claim 9, wherein the heater/vaporizer module is configured to remove moisture from the sample of the gas stream received from the second portion of the sampling probe before the sample of the gas stream received from the second portion of the sampling probe is provided to the detector module.

11. The apparatus of claim 9, wherein the dilution module is configured to dilute the concentration of the particulate matter in the sample of the gas stream received from the second portion of the sampling probe before the sample of the gas stream received from the second portion of the sampling probe is provided to the detector module.

12. The apparatus of claim 9, wherein the water spray module is configured to add moisture to the sample of the gas stream received from the second portion of the sampling probe before the sample of the gas stream received from the second portion of the sampling probe is provided to the detector module.

13. The apparatus of claim 9, wherein the air pulse module is configured to push the sample of the gas stream received from the second portion of the sampling probe with pulses of air to adjust a velocity of the sample of the gas stream received from the second portion of the sampling probe before the sample of the gas stream received from the second portion of the sampling probe is provided to the detector module.

14. The apparatus of claim 7, further comprising an outlet probe that is configured to return the sample of the gas stream received from the second portion of the sampling probe and output from the particulate matter analysis component to the duct.

15. A method, comprising:
diverting a sample of a gas stream from an inner chamber of a duct using a sampling probe, the inner chamber of the duct being configured to carry the gas stream containing the particulate matter therethrough, the sample of the gas stream and the gas stream having a same particulate matter concentration, the sampling probe having a first portion configured to penetrate inside a wall of the duct to the inner chamber and a second portion that extends from the wall of the duct opposite the inner chamber; and
determining a concentration of the particulate matter in the sample of the gas stream received from the second portion of the sampling probe;
wherein the second portion of the sampling probe is configured to direct the sample of the gas stream in a first direction with a second direction corresponding to a direction of the gravitational force of the earth;
wherein a first ray corresponding to the first direction forms an angle $\beta$ with a second ray corresponding to the second direction; and
wherein the angle $\beta$ is less than 90 degrees.

16. The method of claim 15, wherein the angle $\beta$ is less than 80 degrees.

17. The method of claim 15, wherein the angle $\beta$ is less than 45 degrees.

18. The method of claim 15, wherein the angle $\beta$ is approximately 0 degrees.

19. The method of claim 15, wherein the inner chamber of the duct is configured to carry the gas stream in a third direction that is substantially opposite that of the second direction.

20. The method of claim 15, wherein the inner chamber of the duct is configured to carry the gas stream in a third direction that is substantially perpendicular to that of the second direction.

21. The method of claim 15, further comprising:
performing at least of a scattered light measurement analysis on the sample of the gas stream received from the second portion of the sampling probe and a transmissiometry analysis on the sample of the gas stream received from the second portion of the sampling probe.

22. The method of claim 15, further comprising:
removing moisture from the sample of the gas stream received from the second portion of the sampling probe before determining the concentration of the particulate matter in the sample of the gas stream received from the second portion of the sampling probe.

23. The method of claim 15, further comprising:
diluting the concentration of the particulate matter in the sample of the gas stream received from the second portion of the sampling probe before determining the concentration of the particulate matter in the sample of the gas stream received from the second portion of the sampling probe.

24. The method of claim 15, further comprising:
adding moisture to the sample of the gas stream received from the second portion of the sampling probe before determining the concentration of the particulate matter in the sample of the gas stream received from the second portion of the sampling probe.

25. The method of claim 15, further comprising: pushing the sample of the gas stream received from the second portion of the sampling probe with pulses of air to adjust a velocity of the sample of the gas stream received from the second portion of the sampling probe before determining the concentration of the particulate matter in the sample of the gas stream received from the second portion of the sampling probe.

* * * * *